United States Patent [19]

Braden et al.

[11] 4,420,433

[45] Dec. 13, 1983

[54] PROCESS FOR THE PREPARATION OF FLUORINE-SUBSTITUTED CARBOXYLIC ACID CHLORIDES AND THEIR USE

[75] Inventors: Rudolf Braden; Erich Klauke, both of Odenthal, Fed. Rep. of Germany

[73] Assignee: Bayer Aktiengesellschaft, Leverkusen, Fed. Rep. of Germany

[21] Appl. No.: 396,568

[22] Filed: Jul. 9, 1982

[30] Foreign Application Priority Data

Jul. 24, 1981 [DE] Fed. Rep. of Germany ....... 3129274

[51] Int. Cl.³ .............................................. C07C 51/58
[52] U.S. Cl. ........................... 260/544 D; 260/544 Y; 260/544 S; 260/544 B
[58] Field of Search ........... 260/544 D, 544 B, 544 Y, 260/544 S

[56] References Cited

U.S. PATENT DOCUMENTS

| | | | |
|---|---|---|---|
| 944,372 | 12/1909 | Mugdan | 260/544 Y |
| 3,694,499 | 9/1972 | Quarles | 260/544 D |
| 3,706,773 | 12/1972 | Anello et al. | 260/544 Y |
| 3,725,475 | 4/1973 | Paucks | 260/544 Y |
| 4,136,113 | 1/1979 | Johnston | 260/544 Y |

*Primary Examiner*—Paul J. Killos
*Attorney, Agent, or Firm*—Sprung, Horn, Kramer & Woods

[57] ABSTRACT

Fluorine substituted carboxylic acid chlorides are prepared from the corresponding fluorine substituted carboxylic acid fluorides by reaction with silicon tetrachloride, or titanium tetrachloride, optionally in the presence of a catalyst. The so-prepared fluorine substituted carboxylic acid chlorides can in turn be readily converted to fluorine substituted aldehydes by reduction with hydrogen in the presence of palladium as catalyst.

20 Claims, No Drawings

PROCESS FOR THE PREPARATION OF FLUORINE-SUBSTITUTED CARBOXYLIC ACID CHLORIDES AND THEIR USE

The invention relates to a process for the preparation of fluorine-substituted carboxylic acid chlorides and their use for the reduction to the corresponding fluorine-substituted aldehydes.

In the preparation of fluorine-substituted carboxylic acid derivatives, fluorine is introduced as a rule by a reaction in which chlorine atoms are replaced by fluorine atoms. Fluorine can be introduced by this method into aliphatic, aromatic and heterocyclic carboxylic acid derivatives. This replacement reaction necessarily also produces the carboxylic acid fluoride (Houben-Weyl, Volume V/3, pages 122 and 123 (1962)).

For the purpose of reducing a fluorinated carboxylic acid fluoride thus obtained by means of hydrogen in the presence of palladium in a so-called Rosenmund reduction in order to prepare the corresponding aldehydes which are normally only accessible with difficulty, it is necessary to convert the carboxylic acid fluorides into the corresponding carboxylic acid chlorides. A problem arises in the conversion in that the fluorine introduced by a replacement reaction into the aliphatic, aromatic or heterocyclic part of the molecule is likewise again replaced by chlorine, which result is undesirable.

It is known to convert carboxylic acid fluorides into the carboxylic acid chlorides in a two-stage reaction (Chemie u. Technologie aliph. fluororganischer Verbindungen Chemistry and Technology of Aliphatic Fluoro-organic Compounds, page 125, Enke Verlag 1964). First, a carboxylic acid fluoride is hydrolysed to give the carboxylic acid which is then converted by means of thionyl chloride or phosphorus chlorides into the corresponding carboxylic acid chloride. However, this process is complicated.

It is known from U.S. Pat. No. 3,344,193 to prepare the corresponding aldehydes from fluorinated aliphatic dicarboxylic acid chlorides by reduction with hydrogen in the presence of palladium as a catalyst in a so-called Rosenmund reduction. This reaction requires the use of a special palladium/carbon catalyst which has shortly before been used for hydrogenating certain acid chlorides to give 2-hydroxy-3,3,4,4,5,5-hexafluorotetrahydropyran and 4-hydroxy-2,2,3,3,4,4-hexafluorovaleric acid (U.S. Pat. No. 3,344,193, column 3, lines 34–39). Such special catalysts for the hydrogenation of fluorine-substituted carboxylic acid chlorides are very complex and hardly suitable for industrial use.

Known catalyst systems for the Rosenmund reduction are very sensitive towards impurities so that the selectivity and activity of the catalyst decrease rapidly. This causes catalyst consumption to be high.

A process has been found for the preparation of fluorine-substituted carboxylic acid chlorides, which is characterized in that the corresponding fluorine-substituted carboxylic acid fluorides are reacted at an elevated temperature with silicon tetrachloride or titanium tetrachloride, if desired in the presence of a catalyst.

Suitable fluorine-substituted carboxylic acid fluorides for the process according to the invention are compounds of the formula (I)

in which $R^1$ denotes a fluorine-substituted aliphatic, araliphatic or aromatic radical.

According to the invention, an aliphatic radical can be a straight-chain or branched hydrocarbon radical having 1 to 18, preferably 1 to 12, carbon atoms. A lower alkyl radical having 1 to about 6 carbon atoms is a particularly preferred aliphatic radical. The aliphatic radicals are substituted by fluorine. The aliphatic radicals can in general contain 1 to 3 fluorine atoms. In the case of aliphatic radicals which have a longer chain, however, more highly fluorinated alkyl radicals, in particular perfluorinated alkyl radicals are also contemplated. The following fluorinated aliphatic radicals may be mentioned as examples: 3,3,3-trifluoropropyl, perfluoropropyl or perfluoroheptyl.

An aromatic radical is in general an aryl radical, preferably phenyl, biphenyl or naphthyl. The phenyl radical is particularly preferred.

Aromatic radicals are likewise substituted by fluorine or fluorine-containing groups. The aromatic radicals in general contain 1 to 3 fluorine atoms. However, it is also possible to use more highly fluorinated, in particular perfluorinated aromatic radicals.

Fluorine-containing groups can contain, in addition to fluorine, additionally also other halogens, such as chlorine. Examples which may be mentioned here are trifluoromethyl, difluorochloromethyl and fluorodichloromethyl.

The trifluoromethoxy radical and the trifluoromethylthio radical can also be used as fluorine-containing groups.

The aromatic radicals can be substituted, in addition to fluorine, also by other radicals which do not change under the reaction conditions. Examples which may be mentioned here are lower aliphatic radicals ($C_1$ to about $C_6$) or the groups

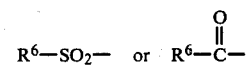

in which $R^6$ denotes a lower alkyl radical ($C_2$ to about $C_6$) or a phenyl radical.

Fluorine-substituted carboxylic acid fluorides of the formula (II)

in which $R^2$ denotes a lower aliphatic radical which is substituted by 1 to 3 fluorine atoms or an aromatic radical

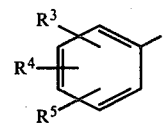

in which $R^3$, $R^4$ and $R^5$ are identical or different and denote trifluoromethoxy, trifluoromethylthio, halogen or a lower aliphatic radical which is unsubstituted or substituted by 1 to 3 halogen atoms, at least one of the radicals $R^3$, $R^4$ or $R^5$ containing fluorine, or denote the groups

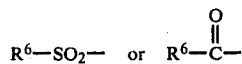

in which $R^6$ has the abovementioned meaning, are particularly preferably used in the process according to the invention.

The following fluorine-substituted carboxylic acid fluorides may be mentioned as examples for the process according to the invention: 2-trifluoromethyl-, 3-trifluoromethyl-, 4-trifluoromethyl-, 4-fluoro-, 2-fluoro-, 2-fluoro-4-trifluoromethyl-, 4-trifluoromethoxy-, 2-fluoro-3-chloro-, 4-fluoro-3-bromo-, 3-fluoro-, 4-fluoro-3-phenoxy-, 4-trifluoromethyl-3-chloro-, 4-phenylsulphonyl-3-trifluoromethyl-, 3-trifluoromethyl-5-trifluoromethoxybenzoyl fluoride, 3,3,3-trifluorobutyric acid fluoride, α-fluorophenylacetic acid fluoride, 3-fluoro-4-methylbenzoyl fluoride, 3-fluoro-4-methoxybenzoyl fluoride, 4-fluorobenzoylacetic acid fluoride, 4-fluorophenoxyacetic acid fluoride, 2-fluorophenylacetic acid fluoride, 4-fluorophenylacetic acid fluoride, α-fluorocinnamic acid fluoride, 4-fluorobutyric acid fluoride, 2,4-difluorobenzoyl fluoride, 3,4-difluorobenzoyl fluoride, 2,5-difluorobenzoyl fluoride, 4-fluorophenylbenzoyl fluoride, perfluorobutyric acid fluoride and perfluorocaprylic acid fluoride.

The preparation according to the invention of fluorine-substituted carboxylic acid chlorides is carried out in the presence of silicon tetrachloride or titanium tetrachloride. It can be advantageous, particularly in the preparation of fluorine-substituted aromatic carboxylic acid chlorides, to carry out the process according to the invention in the presence of a catalyst. The catalysts are consisting of a chloride of the elements aluminum, titanium, antimony, tin or boron.

0.25 to 0.375 mol, preferably 0.25 to 0.3 mol, of silicon tetrachloride or titanium tetrachloride are in general employed per mol of fluorine-substituted carboxylic acid fluoride used. If the process according to the invention is carried out in the additional presence of a catalyst, the amount of catalyst used is in general 0.1 to 2% by weight, preferably 0.5 to 1.2% by weight, relative to silicon tetrachloride. Possible catalysts in addition or alternatively to $AlCl_3$, which is preferably used, are $TiCl_4$, $SbCl_5$, $SnCl_4$ or $BCl_3$.

The preparation of fluorine-substituted carboxylic acid chlorides can be carried out, for example, as follows:

The fluorine-substituted carboxylic acid fluoride and, for example, silicon tetrachloride, and, if desired, a catalyst, are initially introduced into a reaction vessel. The reaction mixture is warmed until the evolution of gas commences. The reaction mixture is maintained until the evolution of gas is complete. Generally, the reaction is effected at a temperature of 0° to 250° C., preferably 30° to 180° C. Pressures of 0.01 bar to 5 bar can be used although atmospheric pressure is preferred. The reaction mixture is worked up by distillation.

It is surprising that in carrying out the process according to the invention the fluorine of the carboxylic acid fluoride is selectively replaced by chlorine. Fluorine bonded to other positions in the molecule remains where it is.

Fluorine-substituted carboxylic acid chlorides thus obtained can be used for the preparation of fluorine-substituted aldehydes by reducing them with hydrogen in the presence of a noble metal hydrogenation catalyst.

Catalysts used in the process according to the invention are noble metal hydrogenation catalysts customary for the Rosenmund reduction, in particular palladium catalysts. The noble metal can be in a finely divided form or applied to a support, such as carbon, aluminum oxide, spinel or barium sulphate.

The catalyst can contain in general 0.5 to 10% by weight, preferably 1 to 6% by weight, of a noble metal.

All those solvents are suitable for use as a solvent in the reduction in which fluorine-containing acid chlorides are soluble and which are not attacked either by hydrogen in the presence of catalysts or by the acid chlorides. The boiling point of the solvents can vary within wide limits. Low-boiling solvents can be used when the reduction is carried out under pressure. Hydrocarbons and ethers are suitable solvents. Examples which may be mentioned are methylcyclohexane, fluorinated hydrocarbons, toluene, xylenes, ethylbenzene, tetralin, tetrahydrofuran and dioxane.

When solvents which are in themselves customary for the Rosenmund reduction are used, regulators are advantageously added, by which the activity of the catalyst is adjusted. Examples of regulators which may be mentioned are "quinoline-sulphur", thiourea or formamides. They are added to the reaction mixture as a rule in a quantity of 0.01 to 1% by weight, relative to the noble metal used.

In a preferred embodiment of the process according to the invention sulphones are used as solvents in the reduction. When sulphones are used as solvents the addition of regulators can surprisingly be dispensed with.

Compounds of the formula (III)

$$R^7\text{-}SO_2\text{-}R^8 \qquad (III)$$

in which $R^7$ and $R^8$ are identical or different and denote alkyl having 1 to 13 carbon atoms, aryl, aralkyl in which the aliphatic part has 1 to 6 carbon atoms, or cycloalkyl having 5 to 7 carbon atoms, or in which $R^7$ and $R^8$ can be linked via 4 to 8 hydrocarbon members to give a cyclic compound, can be used as sulphones in the process according to the invention.

According to the invention, alkyl can here be a straight-chain or branched hydrocarbon radical having 1 to 13 carbon atoms, preferably a lower alkyl radical (1 to about 6 carbon atoms). The following alkyl radicals may be mentioned as examples: methyl, ethyl, propyl, isopropyl, butyl, isobutyl, pentyl, isopentyl, hexyl and isohexyl.

According to the invention, aryl can be phenyl or naphthyl, preferably phenyl.

According to the invention, aralkyl can contain in the aliphatic part 1 to about 6 carbon atoms, preferably 1 to about 2 carbon atoms, and be in the aromatic part phenyl or naphthyl, preferably phenyl. The following aralkyl radicals may be mentioned as examples: benzyl, ethylphenyl, phenylethyl and 4-methylbenzyl.

According to the invention, cycloalkyl can contain 5 to 7 carbon atoms, preferably 5 or 6 carbon atoms.

The following cycloalkyl radicals may be mentioned as examples: cyclobutyl, cyclopentyl, cyclohexyl, cycloheptyl and cyclooctyl.

It is also possible for the two substituents of the sulphone group to be linked via hydrocarbon members, preferably methylene groups, to give a cyclic sulphone.

The radicals mentioned can be substituted by customary radicals. Examples of possible substituents which may be mentioned are lower alkyl (1 to about 6 carbon atoms), halogen, such as fluorine or chlorine, and halogenated lower alkyl groups. The alkyl groups can preferably be substituted by fluorine and/or chlorine and the aryl radicals can preferably be substituted by fluorine, chlorine, lower alkyl and/or fluorinated lower alkyl.

The alkyl, aryl, aralkyl and cycloalkyl radicals can be substituted by one or more radicals, preferably 1 to 3 radicals.

The following sulphones may be mentioned as examples: dimethyl sulphone, methyl ethyl sulphone, diisopropyl sulphone, dibutyl sulphone, diethyl sulphone, thiolane-S-dioxide, diphenyl sulphone, phenyl isobutyl sulphone, phenyl ethyl sulphone, phenyl methyl sulphone, phenyl chloromethyl sulphone, phenyl 4-methylphenyl sulphone, 4-methylphenyl ethyl sulphone, 4-methylphenyl isopropyl sulphone, ethyl benzyl sulphone and 4,4'-bis-chlorophenyl sulphone.

A sulphone which boils at a higher temperature than the aldehyde to be prepared is chosen particularly preferably for the process according to the invention so that the aldehyde can be separated from the reaction mixture after the reduction by distillation and the remaining suspension of the catalyst in the sulphone can be used again for the reduction of fresh acid chloride.

Sulphones for the process according to the invention are in themselves known. They can in general be used in the form of the technical grade. A sulphone for the process according to the invention should be virtually free from water.

In a particularly preferred embodiment of the process according to the invention, the hydrogenation catalyst is treated before or during the reduction with a mixture of carbon monoxide and hydrogen. The noble metal hydrogenation catalyst, for example a supported palladium hydrogenation catalyst, is, in general, treated before the reduction for 5 to 60 minutes within a temperature range from 20° to 100° C. with a stream of hydrogen which contains up to 50% by volume of carbon monoxide. It is also possible to suspend the catalyst in the solvent used for the reduction and to pass through a hydrogen/carbon monoxide mixture. It is likewise possible to carry out the carbon monoxide treatment of the catalyst during the reduction by admixing to the hydrogen up to 10% by volume, preferably less than 1% by volume, of carbon monoxide.

The process according to the invention can be carried out, for example, as follows:

The catalyst and the acid chloride are in general dissolved in the solvent and heated at a temperature in the range from 40° to 180° C., preferably from 80° to 160° C., while hydrogen is being passed through, until the evolution of the hydrogen halide has reached at least 90%, preferably 95%, of theory. The reduction is complete as a rule in less than 5 hours.

It is as a rule advantageous if the concentration of the aldehyde in the solvent does not exceed 50% by weight. The reduction is preferably carried out in such a manner that a final concentration of the aldehyde in the solvent of between 15 and 35% by weight is obtained.

It can also be advantageous first to heat up the catalyst in the solvent to the reaction temperature while hydrogen is being passed through and to add the carboxylic acid chloride thereafter.

The partial pressure of hydrogen during the hydrogenation should be at least 0.5 bar. It can be advantageous to carry out the hydrogenation under a partial pressure of hydrogen of 1 to 3 bars. It is in general not necessary for the partial pressure of hydrogen to be higher than 6 bars.

With the aid of the process according to the invention it is surprisingly possible to prepare fluorine-substituted aldehydes from fluorine-substituted carboxylic acid fluorides. These aldehydes are normally prepared only with difficulty.

Fluorine-substituted aldehydes can be used for pharmaceutic agents and plant-protection agents (German Offenlegungsschrift No. 2,210,687 and German Offenlegungsschrift No. 2,933,979).

EXAMPLE 1

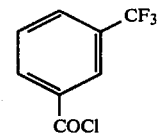

1,000 g of 3-trifluoromethylbenzoyl fluoride, 243 g of $SiCl_4$ (=a molar ratio of 4:1.1) and 2 g of $AlCl_3$ are initially introduced into a three-necked flask equipped with a stirrer and a reflux condenser.

The temperature is increased slowly. At about 60° C. the evolution of gas commences. The mixture is heated up to 160° C. at a rate determined by the decreasing evolution of gas (duration about 4 hours). The temperature is maintained for a further 1 hour at 160° to 170° C. and the batch is then distilled. 929 g of 3-trifluoromethylbenzoyl chloride are obtained; boiling point 77°–8°/20 mbars, $n_D^{20}$ 1.4778.

EXAMPLE 2

In a three-necked flask equipped with a stirrer, a gas inlet tube and a reflux condenser, 250 g of sulpholane (thiolane-S-dioxide), 5 g of Pd-BaSO$_4$ (Pd content: 5% by weight) and 100 g (0.48 mol) of 3-trifluoromethylbenzoyl chloride from Example 1 are heated at 140° C. while hydrogen is being passed through. The elimination of hydrogen chloride which commenced immediately was complete in 3 hours. The 3-trifluoromethylbenzaldehyde formed was distilled off without the catalyst having been filtered off. Boiling point 69°–70° C./20 mbars, $n_D^{20}$ 1.4648, 70 g; Yield: 84% of theory.

It was possible to use the residue of the distillation repeatedly for the reduction in each case of 100 g, of the acid chloride, in the same time. Total yield from 6 batches: 426 g of 3-trifluoromethylbenzaldehyde, which are 85.2%.

EXAMPLE 3

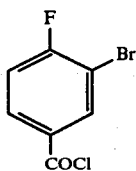

958 g of 3-Br-4-F-benzoyl fluoride, which has a boiling point of 83°/15 mbars and a melting point of 33° C., 184 g of SiCl$_4$ (=a molar ratio of 4:1) and 1.8 g of AlCl$_3$ are initially introduced into a three-necked flask equipped with a stirrer and a reflux condenser and heated up slowly while stirring.

A slow evolution of gas commences at about 30° C. and becomes quite fast at 80° C. After the evolution of gas has abated, heating of the mixture is continued slowly to 175° C. After 6 hours it is worked up and distilled. After light ends of unchanged starting material which can be used again for chlorination have passed over 807 g of 3-bromo-4-fluorobenzoyl chloride (78.4% of theory), which has a boiling point of 117° C./20 mbars and a melting point of 42°–44° C., are obtained.

EXAMPLE 4

2 g of palladium/activated carbon (5% by weight of Pd) and 350 g of toluene are heated for 1 hour at 75° C. in a three-necked flask equipped with a gas inlet tube, a reflux condenser and a stirrer while water gas (CO:H$_2$=1) is being passed through. 70.0 g of 3-bromo-4-fluorobenzoyl chloride prepared as in Example 3 were then added and hydrogen was passed in instead of water gas. The temperature was increased to 85° C. After 4 hours 95% of the amount of hydrogen chloride expected had been split off. After cooling down, the reaction mixture was filtered and the filtrate was distilled off. 53 g of 3-bromo-4-fluorobenzaldehyde, boiling point 112° C./20 mbars, n$_D^{30}$ 1.5685 and melting point: 30° C., were obtained.

A gas chromatogram of the aldehyde showed that it was 98% pure. Yield: 86.8% of theory.

The filtered-off catalyst was used for 3 further reductions of 70.0 g of 3-bromo-4-fluorobenzoyl chloride each. The same yields as for the first batch were achieved.

EXAMPLE 5

In an apparatus as in Example 2, 100 g of 4-trifluoromethylbenzoyl chloride which had been prepared analogously to Example 1 were hydrogenated in the course of 4 hours at 90° C. in 700 ml of dry toluene with the aid of 3.5 g of Pd-carbon (Pd content: 5% by weight); the conversion was 95%. The Pd-carbon catalyst had been exposed, before the hydrogenation, for 30 minutes in toluene at the boil to a mixture containing 50% by volume each of hydrogen and carbon monoxide. By distillation it was possible to obtain 69.2 g of 4-trifluoromethylbenzaldehyde which had a boiling point of 70°–71° C./20 mbars and an n$_D^{20}$ of 1.4639. Yield: 83% of theory.

EXAMPLES 6 to 10

The acid chlorides and aldehydes listed in the table below were prepared analogously to the process used in Examples 1 and 2:

| Examples No. | R | Acid fluoride starting material RCOF | Acid chloride RCOCl | Aldehyde RCHO |
|---|---|---|---|---|
| 5 | 4-Trifluoromethylphenyl | Boiling point 158–159° C. n$_D^{20}$ 1.4399 | Boiling point 82–83° C./23 mbars n$_D^{20}$ 1.4760 | Boiling point 71° C./20 mbars n$_D^{20}$ 1.4640 |
| 6 | 4-Trifluoromethoxyphenyl | Boiling point 60–64° C./18 mbars n$_D^{20}$ 1.4315 | Boiling point 85–86° C./16 mbars n$_D^{20}$ 1.4740 | Boiling point 74°C./19 mbars n$_D^{20}$ 1.4581 |
| 7 | 4-Fluorophenyl | Boiling point 52–53° C./19 mbars n$_D^{20}$ 1.4792 | Boiling point 77° C./21 mbars n$_D^{20}$ 1.5315 | Boiling point 65° C./16 mbars n$_D^{20}$ 1.5211 |
| 8 | 2-Fluoro-3-chlorophenyl | Boiling point 83° C./10 mbars Melting point: 33° C. | Boiling point 110° C./17 mbars n$_D^{20}$ 1.5543 | Boiling point 84° C./15 mbars |
| 9 | 2,6-Difluorophenyl | Boiling point 168° C. Melting point: 36° C. | Boiling point 191° C. n$_D^{20}$ 1.5010 | Boiling point 82–84° C./15 mbars Melting point: 17° C. |
| 10 | 2,6-Fluorochlorophenyl | Boiling point: 79° C./16 mbars n$_D^{20}$: 1.4970 | Boiling point: 90° C./17 mbars n$_D^{20}$: 1.5271 | Boiling point: 104° C./20 mbars Melting point: 32–40° C. |
| 11 | 3,3,3-Trifluoropropyl | Boiling point: 79° C. n$_D^{20}$: 1.3095 | Boiling point: 103° C. n$_D^{20}$: 1.3645 | Boiling point: 94–97° C. n$_D^{20}$: 1.3368 |

COMPARATIVE EXAMPLE A

Example 2 was repeated on 100 g of 3-trifluoromethylbenzoyl chloride which had been obtained by means of thionyl chloride from the corresponding acid. The reduction was complete only after 12 hours as was determined by monitoring the elimination of HCl.

The yield of 3-trifluorobenzaldehyde was 76.6% of theory. The reduction of a further 100 g of the acid chloride using the residue of the distillation could not be completed in the course of 15 hours. The elimination of HCl indicated a conversion of only 76%.

COMPARATIVE EXAMPLE B

In an apparatus as in Example 2, 100 g of 4-trifluoromethylbenzoyl chloride prepared from the acid by means of thionyl chloride, 10 g of a 5% strength palladium-on-barium sulphate catalyst, 1 ml of a 10% strength quinoline-sulphur regulator solution (compare Zmalkowski, loc.cit.) and 700 ml of dry xylene were heated to the boil in a stream of hydrogen. According to the elimination of hydrogen chloride, a conversion of 95% had been reached after 9.5 hours.

After a distillation in vacuo, 60.2 g of 4-trifluoromethylbenzaldehyde were obtained in 95.8% purity, which corresponds to a yield of 69.1%.

What is claimed is:

1. A process for the preparation of a fluorine-substituted carboxylic acid chloride which comprises contacting a fluorine substituted carboxylic acid fluoride at an elevated temperature with silicon tetrachloride or titanium tetrachloride.

2. A process according to claim 1, wherein the process is carried out in the presence of a catalyst consisting of a chloride of aluminum, titanium, antimony, tin or boron.

3. A process according to claim 2, wherein aluminum chloride is the catalyst.

4. A process according to claim 1, wherein the reaction is carried out at a temperature in the range of 0° to 250° C.

5. A process according to claim 1, wherein the fluorine substituted carboxylic acid fluoride is contacted with silicon tetrachloride.

6. A process according to claim 1, wherein the fluorine substituted carboxylic acid fluoride is contacted with titanium tetrachloride.

7. A process according to claim 1, wherein the so-prepared fluorine substituted carboxylic acid chloride is thereafter converted to a fluorine-substituted aldehyde by contact with hydrogen in the presence of a palladium catalyst.

8. A process according to claim 7, wherein the contact of the fluorine substituted carboxylic acid chloride with hydrogen in the presence of a noble metal hydrogenation catalyst is carried out at a temperature in the range of 80° to 160° C.

9. A process according to claim 7, wherein the noble metal hydrogenation catalyst is palladium.

10. A process according to claim 7, wherein the palladium catalyst is one treated with a hydrogen/carbon monoxide mixture.

11. A process according to claim 7, wherein a sulfone as solvent is used.

12. A process according to claim 1, wherein said fluorine-substituted carboxylic acid fluoride is one of the formula

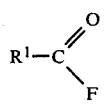
(I)

in which $R^1$ denotes a fluorine-substituted aliphatic, araliphatic or aromatic radical.

13. A process according to claim 1, wherein said fluorine-substituted carboxylic acid fluoride is one of the formula

(II)

wherein $R^2$ denotes a lower aliphatic radical which is substituted by 1 to 3 fluorine atoms or an aromatic radical

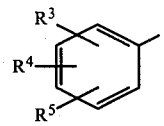

in which $R^3$, $R^4$ and $R^5$ are identical or different and denote trifluoromethoxy, trifluoromethyltio, halogen or a lower aliphatic radical which is unsubstituted or substituted by 1 to 3 halogen atoms, at least one of the radicals $R^3$, $R^4$ and $R^5$ containing fluorine, or denote the groups

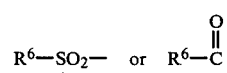

in which $R^6$ denotes a lower alkyl radical of 2 to 6 carbon atoms or a phenyl radical.

14. A process according to claim 1, wherein said fluorine-substituted carboxylic acid fluoride is 3-trifluoromethylbenzoyl fluoride.

15. A process according to claim 1, wherein said fluorine-substituted carboxylic acid fluoride is 4-trifluoromethoxybenzoyl fluoride.

16. A process according to claim 1, wherein said fluorine substituted carboxylic acid fluoride is 4-fluorobenzoyl-fluoride.

17. A process according to claim 1, wherein said fluorine substituted carboxylic acid fluoride is 2-fluoro-3-chlorobenzoyl fluoride.

18. A process according to claim 1, wherein said fluorine substituted carboxylic acid fluoride is 2,6-difluorobenzoyl fluoride.

19. A process according to claim 1, wherein said fluorine substituted carboxylic acid fluoride is 2,6-fluorochlorobenzoyl fluoride.

20. A process according to claim 1, wherein said fluorine substituted carboxylic acid fluoride is 3,3,3-trifluorobutyric acid fluoride.

* * * * *

UNITED STATES PATENT AND TRADEMARK OFFICE
CERTIFICATE OF CORRECTION

PATENT NO. : 4,420,433

DATED : December 13, 1983

INVENTOR(S) : RUDOLF BRADEN and ERICH KLAUKE

It is certified that error appears in the above-identified patent and that said Letters Patent is hereby corrected as shown below:

[30] Foreign Application Priority Data should read
-- Jul. 24, 1981 [DE] Fed. Rep. of Germany......3129273 --.

Signed and Sealed this

Seventeenth Day of April 1984

[SEAL]

Attest:

GERALD J. MOSSINGHOFF

Attesting Officer     Commissioner of Patents and Trademarks